(12) United States Patent
Ivachtchenko et al.

(10) Patent No.: US 9,370,576 B2
(45) Date of Patent: Jun. 21, 2016

(54) PHARMACEUTICAL COMPOSITION HAVING IMPROVED FLOWABILITY, MEDICINAL AGENT, AND METHOD FOR PRODUCING AND USING SAME

(71) Applicants: Alexandre Vasilievich Ivachtchenko, Encinitas, CA (US); ALLA CHEM, LLC, Carson City, NV (US)

(72) Inventors: Alexandre Vasilievich Ivachtchenko, Encinitas, CA (US); Alexandre Viktorovich Demin, Moscow (RU)

( * ) Notice: Subject to any disclaimer, the term of this patent is extended or adjusted under 35 U.S.C. 154(b) by 0 days.

(21) Appl. No.: 14/410,584

(22) PCT Filed: Jul. 5, 2013

(86) PCT No.: PCT/RU2013/000572
§ 371 (c)(1),
(2) Date: Dec. 23, 2014

(87) PCT Pub. No.: WO2014/011083
PCT Pub. Date: Jan. 16, 2014

(65) Prior Publication Data
US 2015/0335754 A1  Nov. 26, 2015

(30) Foreign Application Priority Data
Jul. 11, 2012 (RU) ................................ 2012129101

(51) Int. Cl.
| | |
|---|---|
| *A61K 47/36* | (2006.01) |
| *A61K 47/32* | (2006.01) |
| *A61K 47/10* | (2006.01) |
| *A61K 31/135* | (2006.01) |
| *A61K 9/48* | (2006.01) |
| *A61J 3/07* | (2006.01) |

(52) U.S. Cl.
CPC ............... *A61K 47/36* (2013.01); *A61K 9/4858* (2013.01); *A61K 9/4866* (2013.01); *A61K 31/135* (2013.01); *A61K 47/10* (2013.01); *A61K 47/32* (2013.01); *A61J 3/074* (2013.01)

(58) Field of Classification Search
None
See application file for complete search history.

(56) References Cited

U.S. PATENT DOCUMENTS

2010/0267675 A1 * 10/2010 Ruegger ............... A61K 9/0056
514/114

FOREIGN PATENT DOCUMENTS

| WO | WO 2011/131369 A1 * | 10/2011 | ............... A61K 9/16 |
|---|---|---|---|
| WO | WO 2011/131370 A1 * | 10/2011 | ............... A61K 9/14 |

* cited by examiner

Primary Examiner — Brian J Davis

(57) ABSTRACT

The invention relates to the field of pharmaceutics, in particular, to solid pharmaceutical composition comprising 2-amino-2-[2-(4-octylphenyl)ethyl]propane-1,3-diol or pharmaceutically acceptable salt thereof, stabilizer, lubricant and filler; to method for preparation of pharmaceutical composition, to medicaments for immune suppression and treating multiple sclerosis. 2-Amino-2-[2-(4-octylphenyl)ethyl]propane-1,3-diol represents an immune modulator, which causes redistribution of lymphocytes from blood flow into secondary lymphoid tissue that leads to immune suppression. The invention provides uniform distribution of the active ingredient in the solid composition, high stability and improved flowability of the solid pharmaceutical composition. Due to the improved flowability the compositions suggested in the invention can be used on automated equipment.

15 Claims, No Drawings

PHARMACEUTICAL COMPOSITION HAVING IMPROVED FLOWABILITY, MEDICINAL AGENT, AND METHOD FOR PRODUCING AND USING SAME

FIELD OF INVENTION

The invention relates to the field of pharmacy, in particular, to solid pharmaceutical compositions, comprising 2-amino-2-[2-(4-octylphenyl)ethyl]propane-1,3-diol or its pharmaceutically acceptable salt, stabilizer, lubricant, and filler; to methods for preparation of pharmaceutical composition, to medicaments for immune suppression and treating multiple sclerosis.

BACKGROUND OF THE INVENTION

The present invention provides uniform distribution of the active component in a solid composition, high stability and improved flowability of the solid pharmaceutical composition. Due to improved flowability the compositions suggested in the invention could be used on automatic equipment.

2-Amino-2-[2-(4-octylphenyl)ethyl]propane-1,3-diol in the form of free base or in the form of pharmaceutically acceptable salt, for example, hydrochloride, represents a S1P receptor modulator. Sphingosine-1 phosphate (hereinafter "S1P") is a natural blood serum lipid. Presently there are eight known S1P receptors, namely from Lysophospholipid edg1 to edg8 [http://integrity.thomson-pharma.com]. Modulators or agonists S1P are typically sphingosine analogues, such as 2-substituted 2-amino-propane-1,3-diol or 2-amino-propanol derivatives, e.g. a compound comprising a group of the general formula A [WO 2007/021166],

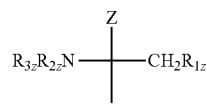

wherein Z represents H, $C_{1-6}$alkyl, $C_{2-6}$alkenyl, $C_{2-6}$alkynyl, phenyl; phenyl, substituted with OH; $C_{1-6}$alkyl, substituted with 1-3 substituents selected from the group consisting of halogen, $C_{3-8}$cycloalkyl, phenyl and phenyl substituted with OH, or $CH_2$—$R_{4z}$, wherein $R_{4z}$ is OH, acyloxy or a residue of a formula A1,

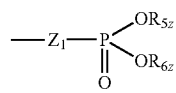

wherein $Z_1$ is a direct bond or O, preferably O; each of $R_{5z}$ and $R_{6z}$, independently, is H, or $C_{1-4}$ alkyl, optionally substituted with 1, 2 or 3 halogen atoms;

$R_{1z}$ is OH, acyloxy or a residue of formula A, and each of $R_{2z}$ and $R_{3z}$, independently, is H, $C_{1-4}$ alkyl or acyl.

S1P receptor modulators are the compounds which act as agonists of one or more sphingosine-1 phosphate receptors, e.g. from S1P1 to S1P8. Agonist binding to S1P receptor may e.g. cause dissociation of intracellular heterotrimeric G-proteins into $G_\alpha$-GTP and $G_{\beta\gamma}$-GTP, and/or increase phosphorylation of the agonist-occupied receptor and activation of downstream signaling pathways/kinases.

As can be seen from various review, the more preferable modulators or agonists of S1P receptors are compounds of the general formula B [EP 627406A1],

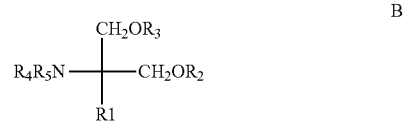

wherein:

$R_1$ is a straight or branched $C_{12-22}$chain, which may have a bond or a heteroatom selected from a double bond, a triple bond, O, S, $NR_6$, wherein $R_6$ is H, $C_{1-4}$alkyl, aryl-$C_{1-4}$alkyl, acyl, $C_{1-4}$alkoxycarbonyl, and carbonyl, and/or which may have such a substituent as $C_{1-4}$alkoxy, $C_{2-4}$alkenyloxy, $C_{2-4}$alkynyloxy, aryl-$C_{1-4}$alkoxy, acyl, $C_{1-4}$alkylamino, $C_{1-4}$alkylthio, acylamino, ($C_{1-4}$alkoxy)carbonyl, ($C_{1-4}$alkoxy)-carbonylamino, acyloxy, ($C_{1-4}$alkyl)carbamoyl, nitro, halogen, amino, hydroxyimino, hydroxyl or carboxy; or $R_1$ represents phenylalkyl, wherein alkyl is a straight or branched ($C_{6-20}$) carbon chain; or phenylalkyl, wherein alkyl is a straight or branched ($C_{1-30}$) carbon chain, wherein the said phenylalkyl is substituted with straight or branched ($C_{6-20}$)carbon chain, optionally substituted with halogen, straight or branched ($C_{6-20}$)alkoxy chain, optionally substituted with halogen, straight or branched ($C_{6-20}$)alkenyloxy, phenyl-$C_{1-14}$alkoxy, halogenphenyl-$C_{1-14}$alkoxy, phenyl-$C_{1-14}$alkoxy-$C_{1-14}$alkyl, phenoxy-$C_{1-14}$alkoxy or phenoxy-$C_{1-14}$alkyl, cycloalkyl substituted with $C_{6-20}$alkyl, heteroaralkyl substituted with $C_{6-20}$alkyl, heterocyclic $C_{6-20}$alkyl or heterocyclic alkyl substituted with $C_{2-20}$alkyl, and wherein the alkyl moiety may have:

in the carbon chain a bond or a heteroatom selected from a double bond, a triple bond, O, sulfinyl, sulfonyl or $NR_6$, wherein $R_6$ is as defined above, and as a substituent $C_{1-4}$alkoxy, $C_{2-4}$alkenyloxy, $C_{2-4}$alkynyloxy, aryl-$C_{1-4}$alkoxy, acyl, $C_{1-4}$alkylamino, $C_{1-4}$alkylthio, acylamino, ($C_{1-4}$alkoxy)carbonyl, ($C_{1-4}$alkoxy)carbonylamino, acyloxy, ($C_{1-4}$alkyl)carbamoyl, nitro, halogen, amino, hydroxy or carboxy; and each of $R_2$, $R_3$, $R_4$ and $R_5$, independently, is H, $C_{1-4}$alkyl or acyl, or a pharmaceutically acceptable salt or hydrate thereof.

In particular, 2-amino-2-[2-(4-octylphenyl)ethyl]propane-1,3-diol of formula 1 (fingolimod) in free form or in the form of pharmaceutically acceptable salt, e.g. hydrochloride, is an immune modulator which causes redistribution of lymphocytes from blood flow into secondary lymphoid tissue that leads to immune suppression. It is widely used for prophylaxis and treating rejection of new organs or transplanted tissue, e.g. for treating heart transplant recipient, lungs, heart-lung, liver, kidney, pancreatic, skin or corneal transplants; and for prophylaxis of graft-versus-host diseases, such as sometimes happen to be after bone-marrow transplantation; for prophylaxis and treating autoimmune diseases, or inflammatory conditions, such as multiple sclerosis, arthritis (for example, rheumatoid arthritis), inflammatory bowel diseases, hepatitis and so on; for prophylaxis and treating viral myocarditis and viral diseases including hepatitis and HIV [as it was mentioned in, e.g. U.S. Pat. No. 5,604,229, WO 1997/024112, WO 2001/001978, U.S. Pat. No. 6,004,565, U.S. Pat. No. 6,274,629, and JP-14316985].

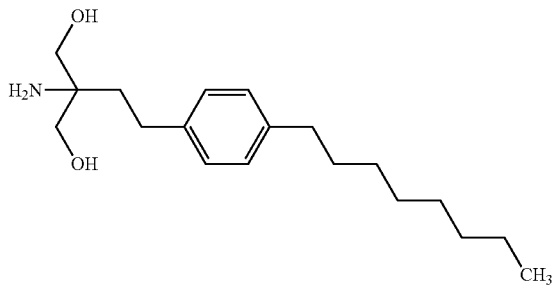

In spite of the fact that 2-amino-2-[2-(4-octylphenyl)ethyl] propane-1,3-diol, first of all in the form of salt, is water soluble, immediately after preparation of the solution or in the course of its storage the crystalline precipitate of this compound is formed. So, a pharmaceutical solution could be preferably used immediately or within short period of time after preparation, e.g. within 4 hours.

It has been determined that addition of cyclodextrins to water solutions of [U.S. Pat. No. 6,476,004] this compound reduces effectively the development of crystalline precipitate, however application of cyclodextrins is limited by their high cost and established standards. Semi-aqueous composition of the compound comprising ethanol and polyethylene glycol is described in EP 0627406. In spite of the fact that crystalline precipitate does not form in semi-aqueous solutions, there are some problems at intravenous administration of the compositions, such as local irritation and hemolysis because of the high concentration of ethanol and polyethylene glycol containing in the composition. There are known various types of liquid concentrates comprising 2-amino-2-[2-(4-octylphenyl)ethyl]propane-1,3-diol [WO 2007/021666 or RU 2402324], predominantly with propylene glycol and, optionally, glycerin. In addition, there is a limitation for medicaments for oral administration to pediatric patients in the sense of smaller number of suitable inert fillers, that is, such composition should preferably be without alcohol.

Thus, the more preferable are solid pharmaceutical compositions comprising 2-amino-2-[2-(4-octylphenyl)ethyl] propane-1,3-diol.

It is known the use of 2-amino-2-[2-(4-octylphenyl)ethyl] propane-1,3-diol in solid pharmaceutical compositions, for example, in WO 2009/048993, wherein fillers are selected from lactose monohydrate, anhydrous lactose, corn starch, mannitol, xylitol, sorbitol, sucrose, microcrystalline cellulose, e.g., Avicel PH 101, dicalcium phosphate, maltodextrin, gelatin; binders are selected from HPMC, L-HPC, Povidone, HPC; disintegrators are selected from corn starch, crospovidone, sodium croscarmellose, sodium carboxymethyl starch, pre-gelatinized starch, calcium silicate; lubricants are selected from hydrogenated castor oil, glyceryl behenate, magnesium stearate, calcium stearate, zinc stearate, mineral oil, silicone fluid, sodium lauryl sulfate, L-leucine, sodium stearyl fumarate, etc.

It is known the use of 2-amino-2-[2-(4-octylphenyl)ethyl] propane-1,3-diol in solid pharmaceutical compositions, for example, in WO 2008/037421, where polymer resins and one or more metal oxides were introduced into composition.

It is known the use of 2-amino-2-[2-(4-octylphenyl)ethyl] propane-1,3-diol in solid pharmaceutical compositions, for example, in RU 2426555, where polyethylene glycol 300 and polysorbate 80 are used in the compositions for treating cancer.

It is also known the use of 2-amino-2-[2-(4-octylphenyl) ethyl]propane-1,3-diol in solid pharmaceutical compositions, for example, in RU 2358716, where a pharmaceutical composition suitable for oral administration comprises 2-amino-2-[2-(4-octylphenyl)ethyl]propane-1,3-diol hydrochloride (FTY-720), sugar alcohol represented by mannitol, magnesium stearate as a lubricant, which is intended for use in the manufacture of a medicament for prophylaxis or treating rejection of new organs or transplant tissue, graft versus host reaction, autoimmune diseases, inflammatory conditions, viral myocarditis and viral diseases related to viral myocarditis, for use in the manufacture of a medicament for treating multiple sclerosis.

When automatic filling machines are used the substances must exhibit some definite physical-chemical and technological properties, such as:
definite size and shape of particles;
uniformity of particle size;
homogeneity of mixing;
flowability (flow);
moisture content;
ability to be compactly formed under pressure.
(Industrial Technology of medicaments. Vol. 2 ed. Chueshova V. I., 2002, p. 407-408).

On retention of sufficiently high parameters of bioavailability of the active component, the disadvantage of the above known solid pharmaceutical compositions of 2-amino-2-[2-(4-octylphenyl)ethyl]propane-1,3-diol is insufficiently high flowability, that does not allow effectively use modern automatic equipment.

DISCLOSURE OF THE INVENTION

The task of the present invention is to provide a new highly effective, solid pharmaceutical compositions on the basis of S1P receptor modulator, representing 2-amino-2-[2-(4-octylphenyl)ethyl]propane-1,3-diol, which is storage-stable, does not cause irritation, non-toxic and at the same time, exhibit improved flowability, to suppress the immune system and treat multiple sclerosis.

The posed task is solved by a novel solid pharmaceutical composition on the basis of S1P receptor modulator, representing 2-amino-2-[2-(4-octylphenyl)ethyl]propane-1,3-diol or a pharmaceutically acceptable salt thereof, and comprising in addition lactulose, polyethylene glycol-6000, and polyvinyl pyrrolidone.

The authors of the present invention have found that the advantages of the new solid pharmaceutical composition with the mentioned proportion of ingredients are the absence of toxicity, lack of allergic reactions, use of components approved for both children and adults, as well as uniform distribution of the active ingredient in the solid composition, high stability.

The technical result of the present invention is a greatly improved flowability of the new solid pharmaceutical composition on the basis of S1P receptor modulator, representing 2-amino-2-[2-(4-octylphenyl)ethyl]propane-1,3-diol, due to which the composition suggested in the invention can be more efficiently used on automated equipment, in particular, for example, to increase the rate of encapsulation with the retention of all pharmacological properties of the pharmaceutical composition, for example, such as binding to receptor S1P. As it will be shown below in the embodiments of the invention, the flowability of a new solid pharmaceutical composition according to the present invention on an average is 4-times as great as the flowability of the chosen prototype FTY-720 Gylenia, the known agent for treating multiple sclerosis (RU 2358716).

In the context of the invention, the terms are generally defined as follows:

"Medicament"—is a compound (or a mixture of compounds representing a pharmaceutical composition) in the form of tablets, capsules, injections, ointments and other drug products intended for restoration, improvement or modification of physiological functions at humans and animals, and for prophylaxis and treatment of diseases, diagnostics, anesthesia, contraception, cosmetology and others.

"Glidant" is a substance, lubricating and preventing sticking. By nature lubricants can be divided into two groups: a) fats and fat-like substances; b) powdery substance. Powdery substances are more applicable then the fat-like ones, because the latter impact on solubility and chemical stability of the tablets. Powdery lubricants are introduced by powdering of granulate. They provide constant-rate outflow of mass for tabletizing from hopper into matrix that guaranties accuracy and constancy of the drug substance dosage. Lubricants facilitate extrusion of tablets from matrix, thus preventing formation of scratches on their surfaces. Anti sticking agents prevent adhesion of the mass to the walls of punches and matrix, as well as adhesion of particles with each other. The preferred lubricants are polyethylene glycol (PEG)-400, polyethylene glycol-6000.

"Stabilizer"—is a component of a pharmaceutical composition, which reduces changes of physical, chemical, pharmacological and other properties of substances at storage or use. Examples of stabilizers include lactulose, polyvinyl pyrrolidone and others.

"Flowability (flow)"—the ability of a powdery system to strew itself out of the tank or funnel or to flow under gravity and to ensure uniform filling of capsules (or matrix channel). A material with a poor flowability sticks to a funnel walls that disturbs the rhythm of its delivery into a capsule. This leads to the fact that the predetermined mass of capsules will vary at automated production. The flowability of powders is a complex characteristic which is determined by the dispersion and shape of particles, mass humidity, particle size distribution and the state of the particle surfaces. This technological characteristic can be used to choose the technology of encapsulation. Powder mixtures containing 80-100% of small fraction (particle size less than 0.2 mm) are dosed in unsatisfactory way, that is why, it is necessary to carry out directional coarsening of the particles of this mass, i.e. granulation.

"Pharmaceutical composition" means a composition comprising an active compound (2-amino-2-[2-(4-octylphenyl) ethyl]propane-1,3-diol according to the present invention), or its pharmaceutically acceptable salt, and, at least, one of the components selected from the group consisting of pharmaceutically acceptable and pharmacologically compatible fillers, solvents, diluents, carriers, auxiliaries, distributing and sensing agents, delivery agents, such as preserving agents, stabilizers the meanings of which are defined in this section, fillers, disintegrators, moisteners, emulsifiers, suspending agents, thickeners, sweeteners, flavoring agents, aromatizing agents, antibacterial agents, fungicides, lubricants, and prolonged delivery controllers, antioxidants, glidants, the meanings of which are defined in this section. The choice and suitable proportions of them are depended on the nature and way of administration and dosage. Examples of suitable suspending agents are: ethoxylated isostearyl alcohol, polyoxyethene, sorbitol and sorbitol ether, microcrystalline cellulose, aluminum metahydroxide, bentonite, agar-agar and tragacant and their mixtures as well. Protection against microorganism action can be provided by various antibacterial and antifungal agents, such as: parabens, chlorobutanol, sorbic acid, and similar compounds.

Examples of suitable excipients using as carriers, solvents, diluents and delivery agents include water, ethanol, polyalcohols and their mixtures, as well as oils. Examples of suitable excipients for making of combinations are glycerol monolinoleate, propylene glycol caprylate, ethoxydiethylene glycol, glycerol trioleate, macrogol, paraffin, macrogol glyceryl ricinoleate, oleic acid, glyceryl monocaprylate, macrogol glyceryl hydroxystearate, macrogol glyceryl linoleate, propylene glycol caprylate, lanoline, linoleoile, poloxamer, propylene carbona, fatty acid glycerides.

When it is necessary to use the pharmaceutical composition according to the present invention in clinical practice it could be mixed for preparation of various forms, at this, it may include traditional pharmaceutical carries. Suitable conventional forms of administration include peroral forms, such as, tablets, gelatinous capsules, pills, powders, granules, chewing gums and oral solutions or suspensions, sublingual and buccal administration forms, aerosols, implants, local, transdermal, subcutaneous, intramuscular, intravenous, intranasal or intraocular administration forms and rectal administration forms. The more preferable form is tablet or gelatin capsule.

Pharmaceutical compositions may include pharmaceutically acceptable excipients (fillers), the meanings of which are defined in this section.

"Pharmaceutically acceptable salt" means relatively non-toxic both organic and inorganic salts of acids and bases disclosed in this invention. These salts can be prepared in situ during the synthesis, isolation or purification of compounds or prepared specially. In particular, the base salts could be prepared especially from the purified free base of the claimed compound and a suitable organic or inorganic acid. Examples of salts thus obtained are hydrochloride, hydrobromide, sulfate, bisulfate, phosphate, nitrate, acetate, oxalate, valerate, oleate, palmitate, stearate, laurate, borate, benzoate, lactate, tosylate, citrate, maleate, fumarate, succinate, tartrate, mesylates, malonates, salicylates, propionates, ethane sulphonates, benzene sulfonates, sulfamates and the like. (Detailed description of such salt properties are given in Berge S. M., et al., "Pharmaceutical Salts" J. Pharm. Sci. 1977, 66: 1-19.). Salts of the disclosed acids may be specially prepared by the reaction of purified acids with suitable base; metal and amine salts may also be synthesized. Metal salts are salts of sodium, potassium, calcium, barium, zinc, magnesium, lithium and aluminum, the most preferable of which are sodium and potassium salts. Suitable inorganic bases from which metal salts can be prepared are sodium hydroxide, carbonate, bicarbonate and sodium hydride, potassium hydroxide and potassium bicarbonate, potassium carbonate, lithium hydroxide, calcium hydroxide, magnesium hydroxide, zinc hydroxide. The more preferable pharmaceutically acceptable salt is hydrochloride.

"Pharmaceutically acceptable excipients (fillers)" Pharmaceutically acceptable excipients mean used in the sphere of pharmaceutics diluents, adjuvants and/or carriers. Filler (excipient) is a substance which is added to a medicament in order to make the latter suitable for oral administration (e.g., tablets). Fillers themselves should not produce any pharmacological effect on human being. Sucrose, lactose, glucose, sodium chloride, starch, sodium bicarbonate, polyvinyl pyrrolidone, and others are used as excipients.

The subject of the present invention is a new solid pharmaceutical composition with improved flowability, suitable for oral administration, comprising a S1P receptor modulator, which is 2-amino-2-[2-(4-octylphenyl)ethyl]propane-1,3-diol, or a pharmaceutically acceptable salt thereof, lactulose, polyethylene glycol-6000, and polyvinyl pyrrolidone.

More preferable is a solid pharmaceutical composition with improved flowability, wherein the pharmaceutically acceptable salt is hydrochloride.

More preferable is a solid pharmaceutical composition with improved flowability, wherein percentage of 2-amino-2-[2-(4-octylphenyl)ethyl]propane-1,3-diol hydrochloride is ranged from 0.01 to 20 mass % based on the mass of the composition.

More preferable is a solid pharmaceutical composition with improved flowability, wherein percentage of 2-amino-2-[2-(4-octylphenyl)ethyl]propane-1,3-diol hydrochloride is ranged from 0.5 to 5 mass %.

More preferable is a solid pharmaceutical composition with improved flowability, wherein percentage of lactulose is ranged from 75 to 99.99 mass %.

More preferable is a solid pharmaceutical composition with improved flowability, wherein percentage of lactulose is ranged from 90 д о 99.5 mass %.

Possessing immunodulatory properties of 2-amino-2-[2-(4-octylphenyl)ethyl]propane-1,3-diol in the free form or in the form of pharmaceutically acceptable salt, e.g. hydrochloride, and the properties of S1P receptor modulator which are known from the above mentioned sources, the pharmaceutical composition with the improved flowability according to the present invention may be used for preparing a medicament intended for treating rejection of transplant organ or tissue, inflammatory conditions, autoimmune and viral diseases, for treating multiple sclerosis.

The subject of the present invention is a medicament in the form of tablet or capsule containing the pharmaceutical composition with improved flowability, placed in a pharmaceutically acceptable packing, preferably gelatinous capsules.

The more preferable is a medicament intended for the prevention or treating rejection of organ or tissue transplant, graft versus host reaction, inflammatory conditions, autoimmune and viral diseases.

The more preferred is a medicament intended for treating multiple sclerosis.

The medicament according to the present invention can efficiently be produced, among other, with the employment of automatic filling machines using the property of improved flowability of the pharmaceutical composition of the present invention.

The subject of the invention is a method for producing a medicament according to the present invention suitable for oral administration, according to which the following ingredients: S1P receptor modulator, which is 2-amino-2-[2-(4-octylphenyl)ethyl]propane-1,3-diol or a pharmaceutically acceptable salt thereof, lactulose, polyethylene glycol-6000, and polyvinyl pyrrolidone are mixed together and placed in a gelatinous capsule, preferably using a capsular filling machine.

The more preferred is a process for preparing the medicament according to the present invention, wherein the pharmaceutically acceptable salt is hydrochloride.

The more preferred is a process for preparing the medicament according to the present invention, according to which percentage of 2-amino-2-[2-(4-octylphenyl)ethyl]propane-1,3-diol hydrochloride is ranged from 0.01 to 20 mass % calculated to the mass of the composition.

The more preferred is a process for preparing the medicament according to the present invention, according to which percentage of 2-amino-2-[2-(4-octylphenyl)ethyl]propane-1,3-diol hydrochloride is ranged from 0.5 to 5 mass %.

The more preferred is a process for preparing the medicament according to the present invention, according to which percentage of lactulose is ranged from 75 to 99.99 mass %.

The more preferred is a process for preparing the medicament according to the present invention, according to which percentage of lactulose is ranged from 90 to 99.5 mass %.

The pharmaceutical composition or medicament of the present invention are administered orally. Moreover clinical dosage of the pharmaceutical composition or medicament according to the present invention could be corrected depending on: therapeutic efficiency and bioavailability of active ingredients in organism, rate of their exchange and removal from organism, and also depending on the age, sex and the severity of the patient's symptoms; the daily intake for adults falls within the range of about 1 to 300 mg, preferably of about 5 to 100 mg. In accordance with the recommendation of physician or pharmacist the above dosage can be taken several times during the definite time intervals (preferably—from one to six times).

THE BEST EMBODIMENT OF THE INVENTION

Below are given specific embodiments of the present invention, examples of the solid pharmaceutical composition with improved flowability, method for its preparation and use which illustrate but not limit the volume of the invention.

EXAMPLE 1

Method for preparing a solid pharmaceutical composition with improved flowability. Lactulose, polyvinyl pyrrolidone (PVP), polyethylene glycol-6000 (PEG-6000) are sifted through a laboratory sieve with a nominal holes diameter of 0.5 mm, placed in containers for row material and weighed on a balance in the amount of:

| | |
|---|---|
| fingolimod hydrochloride | 0.1235 kg; |
| lactulose | 10.4627 kg; |
| PVP | 0.2293 kg; |
| PEG-6000 | 0.2095 kg; |

Carefully, avoiding dust formation the prepared materials are placed in the mixing device CTD-12 in the following amounts:

| | |
|---|---|
| lactulose | 5.4081 kg |
| fingolimod hydrochloride | 0.1223 kg; |
| PVP | 0.2270 kg; |

Mixing time at (10±1) min and rate of stirring at (10±1) r/min were fixed.

Then, the remaining amount of lactulose 4.9500 kg was placed in the mixing device. Mixing time at (15±1) min and rate of stirring at (10±1) r/min were fixed.

Finally, 0.2074 kg of PEG-600 were placed in the mixing device, and mixing time at (3±1) min and rate of stirring (10±1) r/min were fixed.

EXAMPLE 2

By analogy with the method for preparation of solid pharmaceutical composition with improved flowability described in Example 1, the pharmaceutical compositions were prepared in which:

the percentage of 2-amino-2-[2-(4-octylphenyl)ethyl]propane-1,3-diol hydrochloride is ranged from 0.01 to 20 mass %;

the percentage of 2-amino-2-[2-(4-octylphenyl)ethyl]propane-1,3-diol hydrochloride is ranged from 0.5 д о 5 mass %;

the percentage of lactulose is ranged from 75 to 99.99 mass %;

the percentage of lactulose is ranged from 90 to 99.5 mass %.

EXAMPLE 3

Method for preparation of a medicament comprising a pharmaceutical composition with improved flowability. The mass obtained as described in Example 1 was used for encapsulation in a capsule filling machine of stick-slip motion, type Zanasi 25/40 E/F as directed by the instruction.

The average mass of filled capsule is (50±1.0) mg.

EXAMPLE 4

Measurement of flowability for studying the properties of pharmaceutical compositions obtained in Examples 1 and 2. Flowability measurements were carried out on a vibration device VP-12A for characterization of non-cohesive materials. A sample of a pharmaceutical composition (30.0 g) was emptied into a funnel at a closed valve, stop-watch timer was switched on. In 20 sec. the valve was opened, and the flow time of capsule mass was measured. The angle of response was also measured Flowability was calculated by the formula:

$$V_c = \frac{M}{t-20},$$

where: $V_c$ is flowability, g/s;

M—mass of substance, g;

t—time, s.

TABLE 1

Experimental data for measurements of flowability.

| | flowability, g/s | Angle of response, ° |
|---|---|---|
| Percentage of the composition according to the present invention | | |
| 2-amino-2-[2-(4-octylphenyl)ethyl]propane-1,3-diol hydrochloride - 1.1 mass %, lactulose - 94.9 mass %, PVP - 2.1 mass %, PEG-6000 - 1.9 mass %. | 5.4 ± 0.3 | 34 |
| 2-amino-2-[2-(4-octylphenyl)ethyl]propane-1,3-diol hydrochloride - 2.5 mass %, lactulose - 93.5 mass %, PVP - 2.1 mass %, PEG-6000 - 1.9 mass %. | 5.1 ± 0.3 | 36 |
| 2-amino-2-[2-(4-octylphenyl)ethyl]propane-1,3-diol hydrochloride - 5.0 mass %, lactulose - 91.0 mass %, PVP - 2.1 mass %, PEG-6000 - 1.9 mass %. | 4.8 ± 0.3 | 37 |

TABLE 1-continued

Experimental data for measurements of flowability.

| | flowability, g/s | Angle of response, ° |
|---|---|---|
| Percentage of prototype composition (Gylenia) | | |
| 2-amino-2-[2-(4-octylphenyl)ethyl]propane-1,3-diol hydrochloride(FTY-720) - 1.2 mass %, mannitol - 96.8 mass %, magnesium stearate - 2.0 mass %. | 1.4 ± 0.3 | 45 |

The obtained results shown in Table 1 clearly indicate that the solid pharmaceutical composition of the present invention exhibits much better flowability in comparison with prototype.

INDUSTRIAL APPLICABILITY

The invention can be used for medical or pharmaceutical purposes.

The invention claimed is:

1. A pharmaceutical composition with the ability of a powdery system to strew itself out of the tank or funnel or to flow under gravity and to ensure uniform filling of capsules or matrix channel comprising a modulator of S1P receptors representing 2-amino-2-[2-(4-octylphenyl)ethyl]propane-1,3-diol or a pharmaceutically acceptable salt thereof, lactulose, polyethylene glycol-6000, and polyvinyl pyrrolidone.

2. The composition according to claim 1, characterized in that the pharmaceutically acceptable salt is hydrochloride.

3. The composition according to claim 2, characterized in that the percentage of 2-amino-2-[2-(4-octylphenyl)ethyl]propane-1,3-diol hydrochloride is in the range from 0.01 to 20 mass %.

4. The composition according to claim 3, characterized in that the percentage of 2-amino-2-[2-(4-octylphenyl)ethyl]propane-1,3-diol hydrochloride is in the range from 0.5 to 5 mass %.

5. The composition according to any of claims 1-3 characterized in that the percentage of lactulose is in the range from 75 to 99.99 mass %.

6. The composition according to claim 5, characterized in that the percentage of lactulose is in the range from 90 to 99.5 mass %.

7. A medicament in the form of tablet or capsule placed in a pharmaceutically acceptable package comprising a pharmaceutical composition according to claim 1.

8. The medicament according to claim 7 for treatment of rejection of graft or tissue, graft-versus-host reaction, multiple sclerosis.

9. A method for preparation of medicament suitable for oral administration, according to which modulator of S1P receptors representing 2-amino-2-[2-(4-octylphenyl)ethyl]propane-1,3-diol or a pharmaceutically acceptable salt thereof, is mixed together with lactulose, polyethylene glycol-6000, and polyvinyl pyrrolidone, according to claim 7.

10. The method according to claim 9, characterized in that pharmaceutically acceptable salt is hydrochloride.

11. The method according to claim 10, characterized in that the percentage of 2-amino-2-[2-(4-octylphenyl)ethyl]propane-1,3-diol hydrochloride is in the range from 0.01 to 20 mass %.

12. The method according to claim 11, characterized in that the percentage of 2-amino-2-[2-(4-octylphenyl)ethyl]propane-1,3-diol hydrochloride is in the range from 0.5 to 5 mass %.

13. The method according to claim 9, characterized in that the percentage of lactulose is in the range from 75 to 99.99 mass %.

14. The method according to claim 13, characterized in that the percentage of lactulose is in the range from 90 to 99.5 mass %.

15. A method for preparation of medicament suitable for oral administration, according to which modulator of S1P receptors representing 2-amino-2-[2-(4-octylphenyl)ethyl]propane-1,3-diol or a pharmaceutically acceptable salt thereof, is mixed together with lactulose, polyethylene glycol-6000, and polyvinyl pyrrolidone, according to claim 8.

* * * * *